United States Patent [19]

Allard

[11] Patent Number: 4,838,869
[45] Date of Patent: Jun. 13, 1989

[54] RETRACTABLE NEEDLE SYRINGE

[76] Inventor: Edward F. Allard, 7830 Greely Blvd., Springfield, Va. 22152; Daniel Q. Longmire, 3410 Van Dyke St., Alexandria, Va. 22301

[21] Appl. No.: 223,077

[22] Filed: Jul. 22, 1988

Related U.S. Application Data

[63] Continuation of Ser. No. 90,360, Aug. 29, 1987.

[51] Int. Cl.[4] .............................................. A61M 5/32
[52] U.S. Cl. ..................................... 604/195; 604/198
[58] Field of Search ............... 604/195, 194, 198, 187, 604/110, 136

[56] References Cited

U.S. PATENT DOCUMENTS 4,747,831 5/1988 Kulli .................................... 604/198

Primary Examiner—John D. Yasko

[57] ABSTRACT

A retractable hypodermic needle configured for one-time use wherein the needle is spring loaded and automatically irretrievably retracted into the hypodermic syringe when the syringe plunger is fully depressed, whereby protrusions on the end of the plunger engage tabs holding the spring loaded needle to release the needle for retraction.

5 Claims, 4 Drawing Sheets

RETRACTABLE NEEDLE SYRINGE

This application is a continuation-in-part of Ser. No. 090,360 filed Aug. 29, 1987, now abandoned.

BACKGROUND OF THE INVENTION

1. Field of the Invention

This invention relates to hypodermic needles and more specifically to a hypodermic needle which retracts into the syringe after use, thereby preventing reuse and the spread of diseases normally associated therewith.

2. Description of the Prior Art

It is well known that diseases can be spready by re-using a needle and that a person can come in contact with a disease by being accidently scratched by the needle. Hypodermic needles and syringes on the market today have fixed needles attached to a cylinder. After the needle has been used, it should be disabled and destroyed to prevent transmission of diseases.

But, even thrown away needles can expose one to disease as the needle and syringe can quite often be re-used by an unsuspecting person. The contaminated needle can also accidently cut or prick a person, exposing that individual to a transmittable disease. Efforts have been made to educate people not to re-use needles, but the spread of disease through needles is still widespread and hospital personnel have been accidently cut by contaminated needles even though they are extremely careful and well aware of the dangers. Some medical facilities have equipment to break the needle from the syringe or cylinder rendering the syringe harmless, but, these devices are not available to the general public. Some syringes have a protective cap covering the needle which can be placed over the needle after use, allowing the needle to be broken from the syringe, but here again an accidental scratch from the needle could be devastating.

SUMMARY OF THE INVENTION

The present invention effectively overcomes the problems of the prior art and provides for an efficient way of disposing of a spent needle without subjecting one to the potential hazzards of handling it after use while simultaneously removing the needle from circulation, whereby reuse becomes impossible.

DESCRIPTION OF THE PREFERRED EMBODIMENTS

This invention may perhaps be best understood by making reference to several drawings and specifically describing one of the preferred embodiments.

Figure 3:
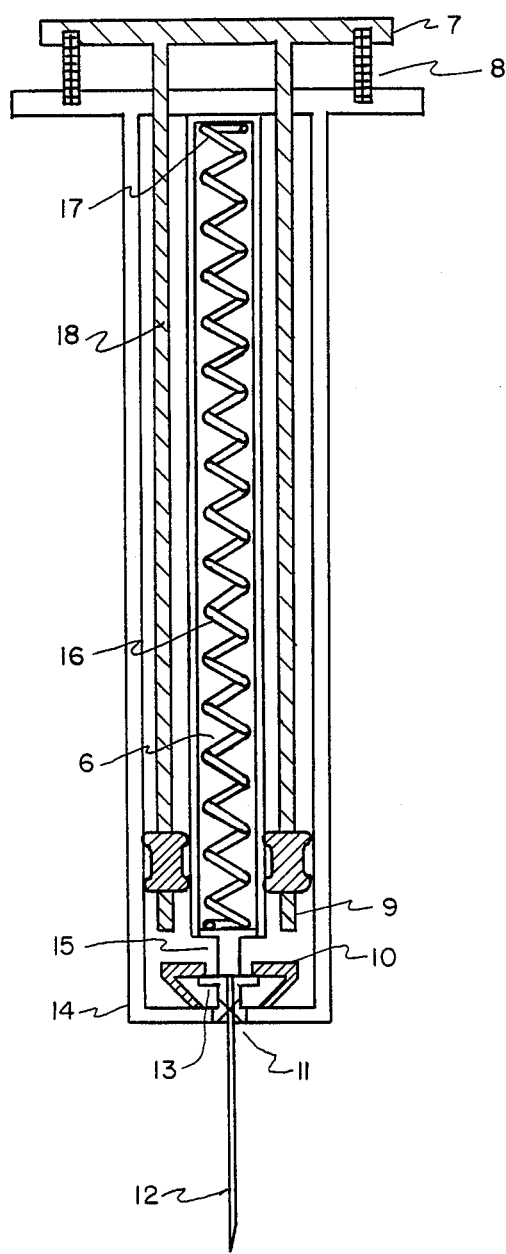
FIG. 3 shows one embodiment of this invention using a spring under tension to retract the spent needle into the syringe.
Figure 4:
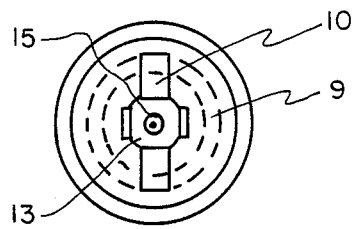
FIG. 4 shows a top cross-sectional view of the hypodermic syringe at Section A—A of FIG. 3.

In the needle's initial state, in FIG. 3, the handle cannot be pushed down. The needle is inserted into a container of fluid and when the handle (7) is pulled back, stop (8) falls off, and the slide or plunger moves away from the needle, thus creating a vacuum to draw fluid from the container into the syringe. When a desired fluid level is reached, the operator stops the pulling process and adjusts the dose. The needle is inserted into a patient or area. Then, the handle (7) is pushed in to force the fluid through the needle. When the slide extensions (9) reach the clamps (10), a push on handle (7) provides a force to release or break the clamps, thus releasing the hold on the needle. The needle is automatically drawing through the gasket (11) and pulled into the inside cylinder (6) where is becomes inaccessible and non-reusable.

Figure 1A:
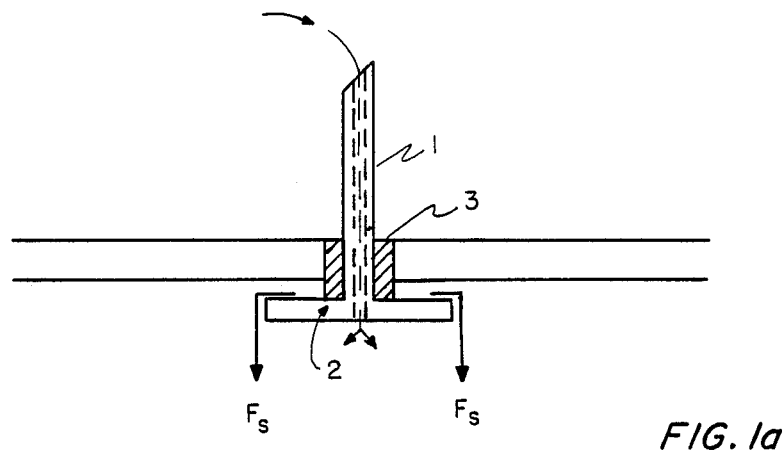
FIGS. 1a, 1b and 1c show various techniques for applying force to the instant retractable needle for securing it within the body of a syringe after use.
Figure 1B:
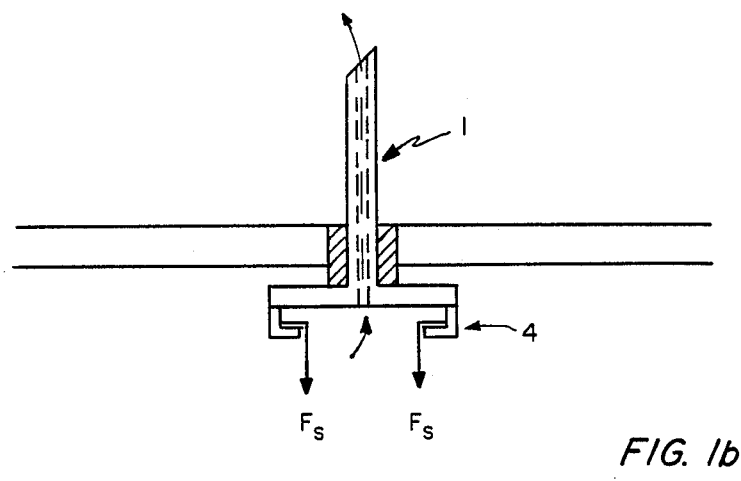
Figure 1C:
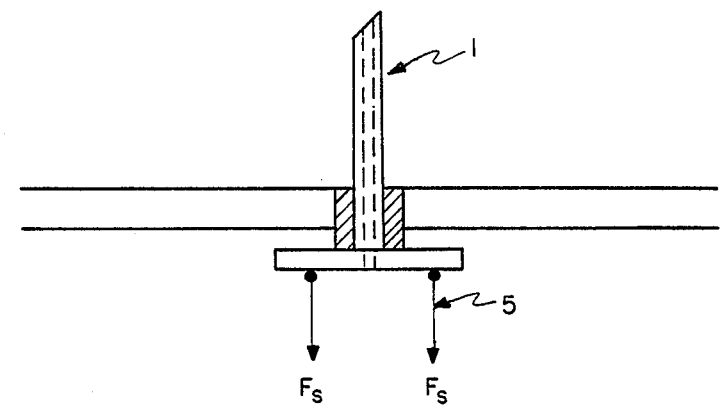
Figure 2A:
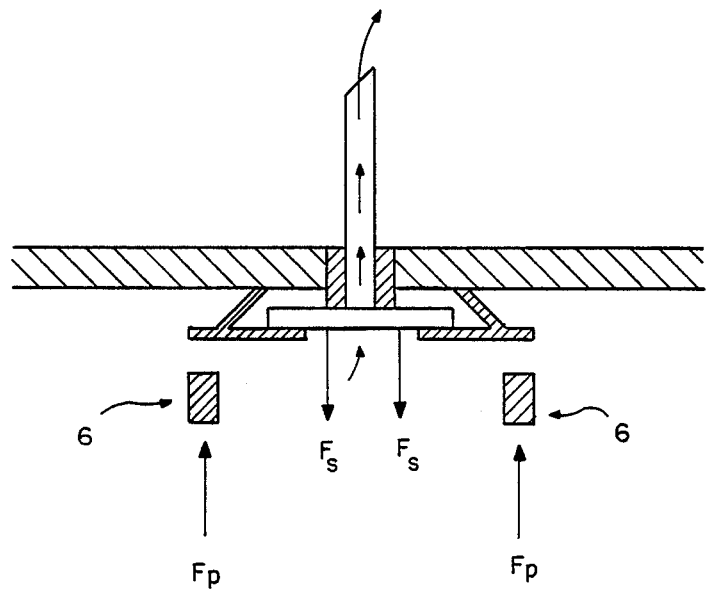
FIGS. 2a and 2b show clamp mechanisms for securely holding the needle in place until released for storage within the syringe.
Figure 2B:
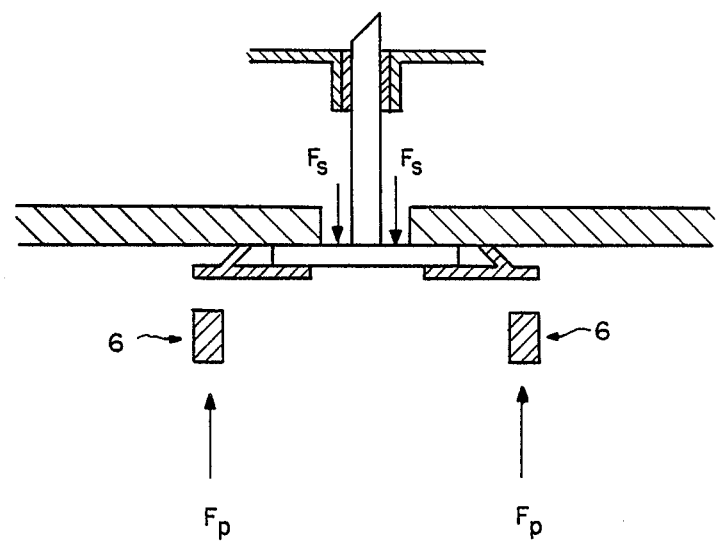

FIG. 3 shows a syringe and needle in its initial state with needle (12) protruding through gasket (11) which serves as a leak-proof seal for the syringe (14) and stabilizes the shaft of the needle (12). In this case the head of the needle (13) is attached to a tensioned spring (16) by an attachment means (15), which can employ any of the means shown in FIGS. 1a, 1b or 1c. The needle is held in place by clamps or tabs (10) fabricated of breakable material or at least a material malleable enough to allow the needle head to be released upon the exertion of force by projections (9) on the end of plunger 18. The tabs (10) can be moulded into the syringe end plate through which the needle protrudes or they could be moulded as part of a washer plate (not shown) which is appropriately seated within syringe body (14). Spring (16) is shown extended and under tension with one end connected to the needle head (13) and the other end connected to the end surface of the inside cylinder (17). In this mechanical state, the needle (12) and head are in mechanical equilibrium wherein the spring force tends to pull the needle through the gasket (11) and the clamp (10) prevents it from being retracted into the body of the syringe. It should be noted here that the syringe is shown in its simplest form with simple finger tabs on the upper and outer portion of the syringe cylinder for holding the syringe, but it should be fully understood that finger tabs are well known in the art and that the handle or plunger cap (7) is thumb actuated and may also contain a lip to extract the plunger from the top of the cylinder during the filling of the syringe.

Figure 7:
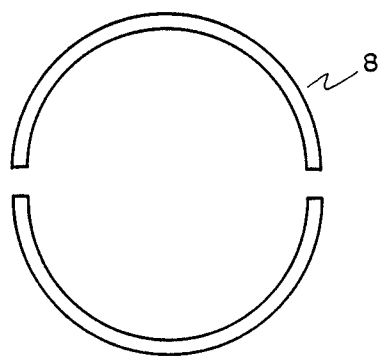
FIG. 7 shows a pair of semi-circular stops placed between the lips of the thumb actuated plunger and the finger hold of the syringe cylinder.

A slide or plunger mechanism (18) has projections (9) on its bottom surface. These projections will release the clamps or tabs (10) when the handle (7) is pushed down. In the initial state, the handle is prevented from being pushed down by a mechanical stop (8). The mechanical stops (8) can be any type of temporary bushing, such as slip rings, or two semi-circlar inserts, as shown in FIG. 7, placed between handle (7) and the top end of syringe housing (14) to assure that the protrusions (9) on the plunger (18) do not release the tabs (10) until the syringe has been used and the needle is ready to be retracted into the inside cylinder (6). The stops (8) are released and fall from their places upon filling the syringe, thus readying the syringe for retraction of the needle upon demand. When the handle is pushed down, the projections (9) release the clamps (10) and attachments (15) pull the needle through gasket (11) and pull the head through the diaphragm (19). Diagraphm (19) prevents liquid from entering the spring cylinder until the diaphragm is broken. The needle and head are then pulled deep into the inside cylinder (12). Once inside the cylinder (6), the needle (12) cannot be again pushed through the gasket by any means, thus rendering the needle inaccessible and non-reuseable.

Figure 5:
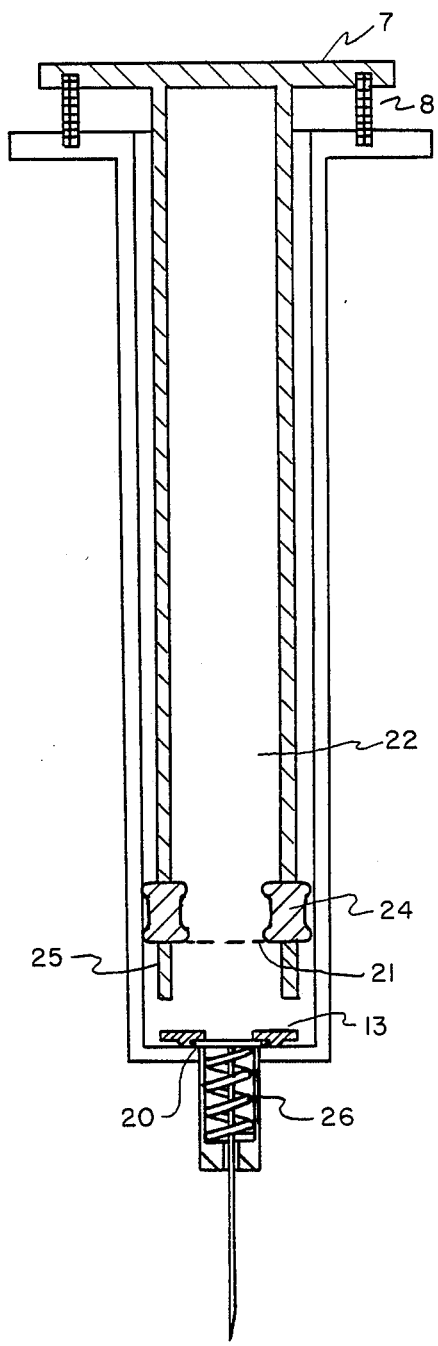
FIG. 5 shows another embodiment of the invention with a spring under compression for forcing the needle into the hollow of the syringe upon release of the holddown tabs.

FIG. 5 shows another arrangement of the invention. In this arrangement, a spring mechanism is under compression in its initial state. Spring force is applied to the needle head (20) tending to drive the head and needle through diaphragm (21) and into chamber (22). In the initial state, clamps (23) hold the needle head from moving up or down. When slide (24) is moved in the direction of the clamps, the projections (25) on the bottom of the slide release the clamps (23) by a release mechanism or by breaking the clamps, thus releasing the needle and needle head. The force of the spring mechanism (26) drives the needle into chamber (22) thereby rendering inaccessible and non-reuseable.

Figure 6:
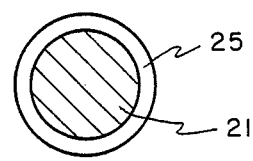
FIG. 6 is a cross-sectional view of FIG. 5 at Section B—B.

FIG. 6 shows a top view of the circular projection (25) and the diaphragm (21). FIG. 7 shows a top view of the circular mechanical stop (8) which prevents the handle (7) of FIGS. 3 and 5 from accidently moving forward and triggering the retraction of the needle. The stop (8) falls from the syringe as the plunger is activated to fill the syringe.

I claim:

1. A hypodermic syringe with a retractable needle comprising outer and inner cylinders, wherein said outer cylinder has a first opening in one end for effecting the protrusion of said retractable needle with a second opening in the other end allowing for the manipulation of a plunger actuator therethrough; said inner cylinder located within the confines of the outer cylinder for receiving and storing the needle when retracted; plunger means in slidable contact with the inner wall of the outer cylinder for effecting a vacuum upon actuating the plunger actuator in an outward direction, whereby a fluid may be drawn into the outer cylinder and expelled upon actuating the plunger inwardly said needle extending through the second opening of the outer cylinder having a head somewhat larger than the diameter of the needle to establish a rim that can be used to firmly hold the needle in place during use by holding tabs within the said other end of the outer cylinder, said needle being spring loaded, whereby upon contacting the holding tabs with the end of the plunger the spring loaded needle is caused to be disengaged and retracted into the inner cylinder for storage.

2. The apparatus of claim 1, wherein the plunger constitutes the inner cylinder with a diaphragm sealing the inner most end of the cylinder and the spring loaded needle is under compression such that upon contact between the plunger hold-down tabs the needle is released and retracted into the inner cylinder for storage.

3. The apparatus of claim 1, wherein the inner cylinder is separate and apart from the outer cylinder and contains a spring under tension, connected to the head of the retractable needle; a plunger slideably engaged between the outer surface of the inner cylinder and the inner surface of the outer cylinder, such that upon compressing the plunger and expelling the fluid the plunger contacts the hold-down tabs, disengages the spring loaded needle and effects the retraction thereof in the inner cylinder for storage.

4. A hypodermic needle wherein the needle is automatically retracted after use for rendering it inaccessible and non-reuseable, comprising a fluid retaining cylinder, a plunger, and a needle; having a front and rear end, the retaining cylinder adapted to hold said needle firmly in place by break away tabs; said plunger being connected to an actuating mechanism outside the fluid retaining cylinder, whereby pressure applied in a push-pull relationship sucks fluid into the retaining cylinder and expels same respectively; upon actuation of the plunger said retaining cylinder having a spring in tension interconnected between the rear end of the needle and opposite end of the retaining cylinder with fluid and expelling same, the plunger strikes said break away tabs, allowing the spring to pull said needle into the confines of the retaining cylinder.

5. The hypodermic needle as recited in claim 4, wherein said spring is enclosed within a cylinder centrally located with the retaining cylinder, whereby when the tabs are broken as recited in claim 4, a spring in compression drives said needle into the confines of the retaining cylinder.

* * * * *